United States Patent [19]
Tamazawa et al.

[11] 4,210,751
[45] Jul. 1, 1980

[54] PROCESS FOR PRODUCING 7β-AMINO-7α-METHOXYCEPHALOSPO-RINS

[75] Inventors: Kazuharu Tamazawa, Shiraokamachi; Takashi Fujikura, Hachioji; Tadao Kojima, Shiraokamachi; Masaru Iwanami, Yokohama, all of Japan

[73] Assignee: Yamanouchi Pharmaceutical Co., Ltd., Tokyo, Japan

[21] Appl. No.: 930,214

[22] Filed: Aug. 2, 1978

[30] Foreign Application Priority Data
Aug. 8, 1977 [JP] Japan .................................. 52/94756

[51] Int. Cl.$^2$ .......................................... C07D 501/18
[52] U.S. Cl. ...................................... 544/21; 424/246
[58] Field of Search .......................................... 544/21

[56] References Cited
U.S. PATENT DOCUMENTS
3,897,424  7/1975  Koller et al. .......................... 544/21

FOREIGN PATENT DOCUMENTS
1445743  8/1976  United Kingdom .

Primary Examiner—Nicholas S. Rizzo
Attorney, Agent, or Firm—Burgess, Ryan and Wayne

[57] ABSTRACT

Process for producing 7β-amino-7α-methoxycephalosporins without the epimerization or formation of the corresponding 7α-amino-7β-methoxy isomers by deacylating cephalosporin derivatives having 7β-acylamino-7α-methoxy group.

7 Claims, No Drawings

PROCESS FOR PRODUCING 7β-AMINO-7α-METHOXYCEPHALOSPORINS

BACKGROUND OF THE INVENTION

1. Field of the Invention

The invention relates to a process for producing 7β-amino-7α-methoxycephalosporins and, more particularly, it relates to a process for producing 7β-amino-7α-methoxycephalosporanic acid compounds from 7β-acylamino-7α-methoxycephalosporanic acid compounds without the accompanying epimerization at the 7-position thereof.

2. Description of the Prior Art

Hitherto, as a process for releasing the acyl group of 7-acylamino-7-methoxycephalosporanic acid compound, there is known a process wherein the cephalosporanic acid compound is reacted with a halogenating agent such as phosphorus pentachloride, etc., to form the corresponding iminohalide and then the iminohalide is reacted with a lower alcohol under anhydrous conditions (see, U.S. Pat. No. 3,956,286). However, in the known process, the reaction is performed at temperatures of from 0° C. to room temperature and the inventor himself clarified that the reaction is accompanied by epimerization to form more than twice the amount of the 7β-methoxy epimer than the 7α-methoxy epimer (see, "Tetrahedron Letters"; No. 14, 1307–1310 (1974)).

In a series of 7-amino-7-methoxycephalosporanic acid compounds, the compounds having antimicrobial activity useful as medicaments are restricted to the 7α-methoxy compounds in which the methoxy group at the 7-position possesses an α-steric configuration but since according to the above-described conventional process, the product is obtained as a mixture of the 7α-methoxy epimer and the 7β-methoxy epimer, it is required to isolate the objective compound from the mixture. It has been pointed out as a difficulty in the conventional process that these epimers are not easily separated from each other.

SUMMARY OF THE INVENTION

The aforesaid difficulty in the conventional process has been overcome by this invention. That is, according to this invention, there is provided a process for producing a 7β-amino-7α-methoxycephalosporanic acid compound represented by the formula

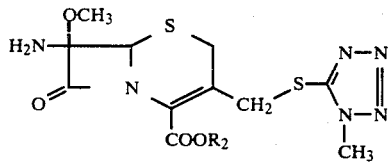

I wherein $R_2$ represents a hydrogen atom or a protective group for the carboxyl group without the accompanying epimerization at the 7-position, which comprises reacting an iminohalide compound or iminoether compound represented by the formula

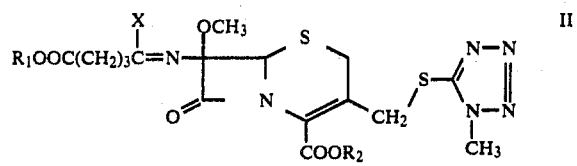

II wherein $R_1$ represents a hydrogen atom or a protective group for the carboxyl group; X represents a halogen atom or a lower alkoxy group; and $R_2$ has the same significance as in the above formula and absolute methanol at temperatures of from −70° C. to −20° C.

DESCRIPTION OF THE PREFERRED EMBODIMENTS

The protective groups ($R_1$ and/or $R_2$) for the carboxyl group used in this invention are the protective groups well known by persons skilled in the art in the field of the cephalosporin chemistry, such as a lower alkyl group, a 2,2,2-trichloroethyl group, a benzyl group, a nitrobenzyl group, a diphenylmethyl group, a triphenylmethyl group, a phenacyl group, etc.

In the process of this invention, the reaction conditions must be controlled with care. In this case, the particularly important reaction condition is the reaction temperature which must be kept lower than −20° C., preferably at −45° C. to −25° C. throughout the reaction. Further, in the case of forming the iminoether compound by adding absolute methanol to the iminohalide compound, the temperature is preferably kept at temperatures of −70° C. to −45° C.

When the reaction of this invention is performed at the temperatures as indicated above, the formation of the 7β-methoxy epimer scarcely occurs or the formation of the 7β-methoxy epimer is, if any, very small compared to that of the conventional process as described before and cause no trouble. On the other hand, when the temperature is kept higher than −20° C., the 7β-epimerization is rapidly accelerated. For example, when the reaction is performed for one hour at −15° C. to −12° C., intermingling of 25% of 7β-methoxy compound is unavoidable (e.g., measured by the formation of 7β-bromoacetamido-7α-methoxycephalosporanic acid compound (shown below), determined by nuclear magnetic resonance spectra).

When the reaction is performed at temperatures below −40° C. using the iminohalide compound as the raw material, the formation of the iminoether compound shown by the formula

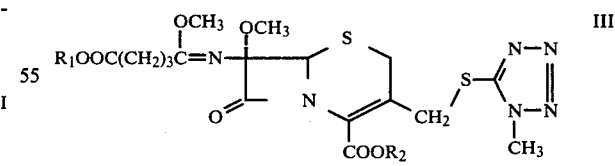

III wherein $R_1$ and $R_2$ have the same significance as in the abovementioned formulae can be confirmed during the reaction. The compound can be easily isolated but by continuing the reaction at the same temperature or by increasing the reaction temperature to about −25° C., the compound in the reaction system can be easily converted into the desired 7β-amino-7α-methoxycephalosporanic acid compound of formula I, by the methanolysis.

The reaction of this invention is carried out in an organic solvent. Any organic solvent which does not take part in the reaction can be used in this invention but chloroform, methylene chloride, ethylene chloride, tetrahydrofuran, etc., which do not contain water are usually used as the organic solvent. The reaction may proceed under about neutral condition but can be accelerated in the presence of an acid.

The objective compound of this invention thus formed can be isolated from the reaction mixture by dispersing the reaction mixture usually cooled below −20° C. in a cooled basic aqueous solution such as an aqueous sodium hydrogencarbonate solution, etc., recovering and drying the organic layer formed, and then subjecting the residue to chromatography.

Thus, from 7β-acylamino-7α-methoxycephalosporanic acid compounds, the corresponding 7β-amino-7α-methoxycephalosporanic acid compounds can be obtained almost without the accompaning epimerization at the 7-position.

The objective compounds of this invention are useful as intermediates for producing various compounds in the amino group at the 7-position. By reacting the objective compounds of this invention and an acylating agent at temperatures below −20° C., 7β-acylamino-7α-methoxycephalosporanic acid compounds can be obtained without the accompaning epimerization at the 7-position. Among these 7β-acylamino-7α-methoxycephalosporanic acid derivatives, some compounds which show excellent antimicrobial activity as semi-synthetic 7α-methoxycephalosporins are included, and also certain intermediates for preparing semi-synthetic 7α-methoxycephalosporins having excellent antimicrobial activity are included. For example, the 7β-bromoacetamido-7α-methoxycephalosporanic acid compounds shown by the formula

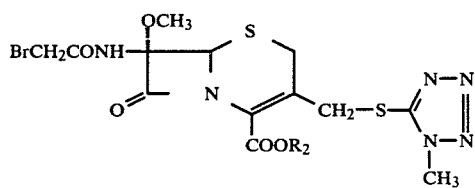

wherein R₂ has the same significance as above, are obtained using bromoacetyl halide as the acylating agent in the aforesaid reaction, are particularly important as intermediates since it is convenient in such compounds to replace the bromine atom with other various atomic groups.

And also, by acylating the compound (1), the cephalosporin compounds having antibacterial properties and being useful as antibiotics are obtained, for example, as follows;

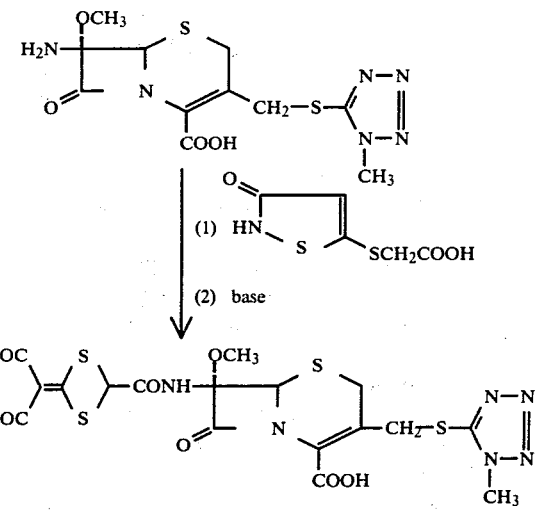

Then, the process of this invention will further be explained in more detail by the following examples.

REFERENCE EXAMPLE 1

In a mixture of 5 ml. of acetone and 5 ml. of dichloromethane was suspended 472 mg. of 7β-(4-carboxybutyramido)-7α-methoxy-3-(1-methyl-1H-tetrazol-5-yl) thiomethyl-Δ³-cephem-4-carboxylic acid (1) and after adding thereto 388 mg. of diphenyldiazomethane, the mixture was stirred overnight at room temperature. Then, the solvent was distilled off under reduced pressure and the residue formed was dried overnight over phosphorus pentoxide to provide 804 mg. of the bis(diphenylmethyl) ester (2) of compound (1). The ester (2) was dissolved in 8 ml. of anhydrous dichloromethane and after successively adding 243 μl. of anhydrous pyridine and 416 mg. of phosphorus pentachloride to the solution under ice-cooling, the mixture was stirred for several minutes at the same temperature and then for 1.5 hours at room temperature. The reaction mixture was cooled to −70° C. to −60° C. and after adding dropwise 1 ml. of absolute methanol to the reaction mixture, the resultant mixture was stirred for 1.5 hours at the same temperature. Then, after adding 1.65 ml. of pyridine to the mixture at −70° C. to −60° C., the reaction mixture obtained was dispersed in ice-water. The organic layer formed was washed twice each time with water, 1 normal hydrochloric acid, and water successively and dried over anhydrous magnesium sulfate. The solvent was distilled off, the residue was subjected to a column chromatography using 13 g. of silica gel, and 402 mg. of oily 7α-methoxy-7β-(1-methoxy-4-diphenylmethyloxycarbonylbutylidene)amino-3-(1-methyl-1H-tetrazol-5-yl)-thiomethyl-Δ³-cephem-4-carboxylic acid diphenylmethyl ester was obtained from the fractions eluted with a 19:1 mixture of benzene and ethyl acetate.

Nuclear magnetic resonance spectra (CDCl₃)

| δ(ppm): | 1.94 | (m, 2H, —CH₂CH₂CH₂—) |
|---|---|---|
| | 2.48 | (t, J = ~ 7Hz, 2H, —OCOCH₂—) |
| | 2.62 | (t, J = ~ 7Hz, 2H, —CH₂—C(OCH₃)=N—) |
| | 3.42 | (s, 3H, C₇—OCH₃) |

-continued

| 3.69 | (s, 3H, $-\overset{\overset{\displaystyle OCH_3}{|}}{C}=N-$) |
| --- | --- |
| 3.78 | (s, 3H, $\diagdown\mkern-10mu N-CH_3$) |
| 4.98 | (s, 1H, $C_6-H$) |
| 6.88<br>6.92 | (s, 1H, $-O-CH\diagup\diagdown$) |

EXAMPLE 1

In 8 ml. of anhydrous dichloromethane was dissolved 804 mg. of the ester (2) obtained in Reference example 1, that is, 7β-(4-diphenylmethyloxycarbonyl-butyramido)-7α-methoxy-3-(1-methyl-1H-tetrazol-5-yl)thiomethyl-$\Delta^3$-cephem-4-carboxylic acid diphenylmethyl ester. Under ice-cooling, 243 μl. of anhydrous pyridine and 416 mg. of phosphorus pentachloride were added to the solution and after several minutes, the ice-water bath was removed and the mixture was stirred for 1.5 hours at room temperature. Thereafter, to the reaction mixture thus formed was added dropwise, 1 ml. of absolute methanol at $-70°$ C. to $-60°$ C., whereby the iminoether compound formed. After the addition of methanol was over, the resultant mixture was stirred for 1.5 hours at $-30°$ C. to $-25°$ C. and the reaction mixture was dispersed in a cold aqueous sodium hydrogencarbonate solution. The organic layer formed was recovered, washed with water, and dried over anhydrous magnesium sulfate. The solvent was distilled off under reduced pressure and the residue was subjected to a silica gel colum chromatography, and 368 mg. of caramel-like 7β-amino-7α-methoxy-3-(1-methyl-1H-tetrazol-5-yl)thiomethyl-$\Delta^3$-cephem-4-carboxylic acid diphenylmethyl ester was obtained from the fractions eluted with a 4:1 mixture of benzene and ethyl acetate.

Nuclear magnetic resonance spectra (CDCl$_3$):

| δ (ppm): | 3.49 | (s, 3H, $C_7-OCH_3$) |
| --- | --- | --- |
| | 3.82 | (s, 3H, $\diagdown\mkern-10mu N-CH_3$) |
| | 4.84 | (s, 1H, $C_6-H$) |
| | 6.93 | (s, 1H, $-OCH\diagup\diagdown$) |

EXAMPLE 2

In 8 ml. of anhydrous dichloromethane was dissolved 804 mg. of the ester (2) obtained in Reference example 1, that is, 7β-(4-diphenylmethyloxycarbonyl-butyramido)-7α-methoxy-3-(1-methyl-1H-tetrazol-5-yl)thiomethyl-$\Delta^3$-cephem-4-carboxylic acid diphenylmethyl ester and the solution was cooled by an ice-water bath. To the solution thus cooled were added 243 μl. of anhydrous pyridine and 416 mg. of phosphorus pentachloride. After several minutes, the ice-water bath was removed, and the mixture was stirred for 1.5 hours at room temperature. The reaction mixture containing the iminohalide thus formed was cooled to $-70°$ C. to $-60°$ C. and 1 ml. of absolute methanol was added to the reaction mixture with stirring. The mixture was, then, kept at $-40°$ C. to $-25°$ C. for 1.5 hours and dispersed in a cold aqueous sodium hydrogencarbonate solution. The organic layer formed was recovered, washed with a cold aqueous sodium hydrogencarbonate solution and then water, and dried with anhydrous magnesium sulfate. After 30 minutes, the drying agent was filtered off and to the filtrate containing 7β-amino-7α-methoxy-3-(1-methyl-1H-tetrazol-5-yl)thiomethyl-$\Delta^3$-cephem-4-carboxylic acid diphenylmethyl ester, which is also one of the objective compounds of this invention, was added dropwise 158 mg. of bromoacetyl chloride at a temperature below $-20°$ C. After several minutes, the reaction mixture was dispersed in ice water and the organic layer formed was recovered, washed with 1 normal hydrochloric acid and then water, and dried over anhydrous magnesium sulfate. The solvent was distilled off and the residue was mixed with benzene and allowed to stand for several minutes, whereby colorless crystals precipitated. The crystals were recovered by filtration and washed with benzene to provide 7β-bromoacetamido-7α-methoxy-3-(1-methyl-1H-tetrazol-5-yl)thiomethyl-$\Delta^3$-cephem-4-carboxylic acid diphenylmethyl ester. By drying the product overnight over phosphorus pentoxide, 583 mg. of the objective compound was obtained.

Melting point: 146–147° C. (decompd.)

Elemental analysis for $C_{26}H_{25}N_6O_5BR\cdot C_6H_6$:

| | C | H | N | Br |
| --- | --- | --- | --- | --- |
| Calculated: | 53.11% | 4.32% | 11.61% | 11.04% |
| Found: | 53.02% | 4.43% | 11.36% | 10.92% |

Determination of benzene by gas chromatography:
Calculated: 10.79% Found: 10.62%

Nuclear magnetic resonance spectra (CDCl$_3$):

| δ (ppm): | 3.57<br>3.78 | (s, 5H, $-OCH_3$, $C_2-H$) |
| --- | --- | --- |
| | | (s, 3H, $\diagdown\mkern-10mu N-CH_3$) |
| | 3.88 | (s, 2H, $BrCH_2CO-$) |
| | 4.04 | (s, 1H, $C_6-H$) |
| | 4.35 | (q, 2H, $C_3-CH_2S-$) |
| | 6.92 | (s, 1H, $-OCH\diagup\diagdown$) |
| | 7.36 |  |

EXAMPLE 3

In 6.5 ml. of dichloromethane was dissolved 655 mg. (1 millimole) of 7α-methoxy-7β-(4-methoxy-d$_3$-carbonylbutyramido)-3-(1-methyl-1H-tetrazol-5-yl)thiomethyl-$\Delta^3$-cephem-4-carboxylic acid diphenylmethyl ester and after adding thereto 242 μl. (3 millimoles) of pyridine and 416 mg (2 millimoles) of phosphorus pentachloride under ice-cooling, the mixture was stirred for 1.5 hours at room temperature. To the reaction mixture containing the iminohalide thus formed was added 242 μl. (3 millimoles) of pyridine at $-60°$ C. to $-50°$ C. and then 1 ml. (26.4 millimoles) of absolute methanol was added dropwise to the mixture at a temperature below −60° C., whereby the iminoether formed. The solution formed was stirred for 1.5 hours at −30° C. to −25° C. (the same experiment was repeated, for the sake of comparison, in the case of stirring for one hour at −20° C. to −17° C. and the case of stirring for one hour at −15° C. to −12° C.), whereby the iminoether once formed caused methanolysis to form 7β-amino-7α-methoxy-3-(1-methyl-1H-tetrazol-5-yl)thiomethyl-Δ³-cephem-4-carboxylic acid diphenylmethyl ester, which is also one of the objective compounds of this invention. The reaction mixture containing the objective compound was cooled again, 1.33 ml. (16.47 millimoles) of pyridine was added thereto at −70° C. to −60° C., and then 1.56 ml. (18.8 millimoles) of bromoacetyl chloride was added dropwise to the mixture at the same temperature. After stirring for several minutes, the reaction mixture was dispersed in ice water, the organic layer formed was recovered, washed twice with cold water, once with a cold aqueous sodium hydrogencarbonate solution, three times with cool water, and then once with saturated aqueous sodium chloride solution, and dried with anhydrous magnesium sulfate. The solvent was distilled off under reduced pressure and the residue was applied to a column chromatography using silica gel and benzene, developed with benzene, and eluted with a 9:1 mixture of benzene and ethyl acetate. Thus, from the eluate, caramel-like 7β-bromoacetamido-7α-methoxy-3-(1-methyl-1H-tetrazol-5-yl)thiomethyl-Δ³-cephem 4-carboxylic acid diphenylmethyl ester was obtained.

In the example, the yield for the objective product and the content of the 7β-epimer determined by the nuclear magnetic resonance spectra for the aforesaid three cases at different reaction temperatures and reaction times in the iminoetherification are shown in the following table.

|   | Methanolysis temperature | Reaction time | 7β-Epimer | Yield |
|---|---|---|---|---|
| (a) | −30° C. to −25° C. | 1.5 hrs. | <5% | 85% |
| (b) | −20° C. to −17° C. | 1.0 hr. | 10% | 78% |
| (c) | −15° C. to −12° C. | 1.0 hr. | 25% | 79% |

The objective compound obtained by recrystallizing the product in case (a) of the above table showed a melting point of 138–140° C. (decompd.).

REFERENCE EXAMPLE 2

In 1.3 ml. of anhydrous dichloromethane was dissolved 130.4 mg. of 7α-methoxy-7β-(4-methoxycarbonylbutyramido)-3-(1-methyl-1H-tetrazol-5-yl)thiomethyl-Δ³-cephem-4-carboxylic acid diphenylmethyl ester. Under ice-cooling, 24 μl. of pyridine and 45.8 mg. of phosphorus pentachloride were added successively to the solution and after several minutes, the mixture was stirred for 1.5 hours at room temperature. The reaction mixture was evaporated to dryness under reduced pressure, the residue formed was extracted with anhydrous benzene, and insoluble materials were filtered off from the extract. The benzene solution obtained was concentrated to dryness under reduced pressure to provide caramel-like 7β-(1-chloro-4-methoxycarbonylbutylidene)amino-7α-methoxy-3-(1-methyl-1H-tetrazol-5-yl)thiomethyl-Δ³-cephem-4-carboxylic acid diphenylmethyl ester. The amount of the product thus obtained was 110 mg.

Nuclear magnetic resonance spectra (CDCl₃):

| δ (ppm): | 2.00 | (m, 2H, −CH₂CH₂CH₂−) |
|---|---|---|
| | 2.40 | (t, J = ~ 7Hz, −OCOCH₂−) |
| | 2.81 | (t, J = ~ 7Hz, −CH₂C(Cl)=N−) |
| | 3.62 3.82 | (s, 3H, −OCH₃ of side chain) |
| | | (s, 3H, \N−CH₃/) |
| | 5.07 | (s, 1H, C₆−H) |
| | 5.32 | (s, 3H, C₇−OCH₃) |
| | 6.90 | (s, 1H, −OCH(/\)) |

EXAMPLE 4

In 1 ml. of anhydrous dichloromethane was dissolved 100 mg. of 7β-(1-chloro-4-methoxycarbonylbutylidene)amino-7α-methoxy-3-(1-methyl-1H-tetrazol-5-yl)thiomethyl-Δ³-cephem-4-carboxylic acid diphenylmethyl ester prepared in Reference example 2 and after adding 0.5 ml. of absolute methanol to the solution at a temperature below −60° C., the resultant mixture was stirred for 1.5 hours at the same temperature. The reaction mixture was dispersed in ice water containing sodium hydrogencarbonate and extracted with dichloromethane. The organic layer was recovered, dried over anhydrous magnesium sulfate, and subjected to a silica gel column chromatography. From the fractions eluted with a 9:1 mixture of benzene and ethyl acetate, 80 mg. of oily 7α-methoxy-7β-(1-methoxy-4-methoxycarbonylbutylidene)amino-3-(1-methyl-1H-tetrazol-5-yl)thiomethyl-Δ³-cephem-4-carboxylic acid diphenylmethyl ester was obtained.

Nuclear magnetic resonance spectra (CDCl₃):

| δ (ppm): | 1.94 | (m, 2H, −CH₂CH₂CH₂−) |
|---|---|---|
| | 2.36 | (t, J = ~ 7Hz, 2H, −OCOCH₂−) |
| | 2.62 | (t, J = ~ 7Hz, 2H, −CH₂C(=O)=N−) |
| | 3.42 | (s, 3H, C₇−OCH₃) |
| | 3.64 | (s, 3H, −COOCH₃) |
| | 3.69 | (s, 3H, −C(OCH₃)=N−) |
| | 3.78 | (s, 3H, \N−CH₃/) |
| | 4.98 | (s, 1H, C₆−H) |
| | 6.92 | (s, 1H, −OCH(/\)) |

EXAMPLE 5

In 1 ml. of anhydrous dichloromethane was dissolved 100 mg. of 7β-(1-chloro-4-methoxycarbonylbutylidene)amino-7α-methoxy-3-(1-methyl-1H-tetrazol-5-yl)thiomethyl-Δ³-cephem-4-carboxylic acid diphenylmethyl ester prepared in Reference example 2 and after adding 0.5 ml. of absolute methanol to the solution at a temperature below −60° C., the mixture was stirred for 1.5 hours at −70° C. to −60° C., whereby the iminoether, i.e., the objective compound in Example 4 formed. Then, the mixture was kept at −30° C. to −25° C. for 1.5 hours to perform the reaction and the reaction mixture was treated as in Example 1 to provide 75 mg. of 7β-amino-7α-methoxy-3-(1-methyl-1H-tetrazol-5-yl)thiomethyl-Δ³-cephem-4-carboxylic acid diphenylmethyl ester.

The values of the nuclear magnetic resonance spectra of the product coincided with those of the compound obtained in Example 1.

What is claimed is:

1. A process for producing a 7β-amino-7α-methoxycephalosporanic acid compound of the formula

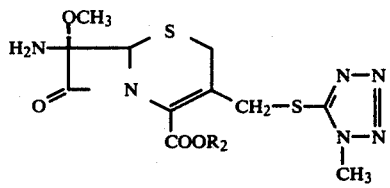

wherein R₂ represents a hydrogen or a protective group for the carboxyl group which comprises reacting an iminohalide compound or an iminoether compound of the formula

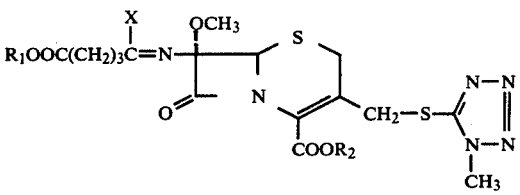

wherein $R_1$ and $R_2$ each represents a hydrogen atom or a protective group for the carboxyl group and X represents a halogen atom or a lower alkoxy group and absolute methanol at −70° C. to −20° C.

2. The process as claimed in Claim 1 wherein said protective group for the carboxyl group in the formulae is a lower alkyl group, a 2,2,2-trichloroethyl group, a benzyl group, a nitrobenzyl group, a diphenylmethyl group, or a triphenylmethyl group.

3. The process as claimed in claim 1 wherein the reaction is carried out in an organic solvent.

4. The process as claimed in claim 3 wherein the organic solvent is chloroform, methylene chloride, ethylene chloride, or tetrahydrofuran.

5. A process according to claim 1 wherein the reaction is conducted between −45° C. and −25° C.

6. A process according to claim 1 wherein, in the formation of the iminoether by addition of absolute methanol to the iminohalide, the temperature is maintained between −70° C. and −45° C.

7. A process according to claim 1, wherein, in the addition of the absolute methanol to the iminoether, the reaction is conducted between −30° C. and −25° C.

* * * * *